United States Patent [19]
Deruyter et al.

[11] Patent Number: 6,032,488
[45] Date of Patent: Mar. 7, 2000

[54] METHOD OF MANUFACTURING A POROUS INHOMOGENEOUS MATERIAL

[75] Inventors: Christian Deruyter, Rueil-Malmaison; Jean-Claude Moulu, Aubergenville; Francois Kalaydjian, Rueil-Malmaison, all of France

[73] Assignee: Institut Francais du Petrole, Ruiel-Malmaison, France

[21] Appl. No.: 08/854,183

[22] Filed: May 9, 1997

[30] Foreign Application Priority Data

May 9, 1996 [FR] France .................................. 96 05888

[51] Int. Cl.[7] .......................... C03B 19/01; C03B 19/09; C03B 23/20; C03B 19/08
[52] U.S. Cl. ............................... 65/17.3; 65/17.5; 65/22; 65/36; 65/144; 55/523; 210/496; 210/510.1; 264/109; 264/126
[58] Field of Search ..................... 65/17.3, 17.5, 65/22, 102, 111, 144, 36, 43; 264/642, 628, 125, 109, 112; 55/487, 523, DIG. 5; 210/500.26, 496, 510.1

[56] References Cited

U.S. PATENT DOCUMENTS

| | | |
|---|---|---|
| 1,117,601 | 11/1914 | Porter . |
| 1,823,356 | 9/1931 | Frink . |
| 2,837,873 | 6/1958 | Lynsavage . |
| 3,249,466 | 5/1966 | Lusher . |
| 4,088,576 | 5/1978 | Mott . |
| 4,186,100 | 1/1980 | Mott . |
| 4,436,538 | 3/1984 | Tomita et al. . |
| 4,629,483 | 12/1986 | Stanton . |
| 5,297,420 | 3/1994 | Gilliland et al. . |
| 5,773,103 | 6/1998 | Ciora, Jr. et al. . |

FOREIGN PATENT DOCUMENTS

| | | |
|---|---|---|
| 0 228 631 | 7/1987 | European Pat. Off. . |
| 59-223278 | 12/1984 | Japan . |
| 603 211 | 8/1978 | Switzerland . |

OTHER PUBLICATIONS

WPI Database Section CH, Week 8505 Derwent Publications, Ltd, London, GB; Class LO1, AN 85–028320 XP002024598 & JP–A–59 223 278 (INA Seito KK), Dec. 15, 1984.

Revue de l'Institut Francais Du Petrole, vol. 47, No. 5, Sep. 1, 1992, pp. 685–701, XP000315205 Fassi–Fihri O. et al: "Study of Wettability of Reservoir Rock on Pore Scale by Scanning . . . Cryomicroscopy".

Aliche Journal, vol. 23, No. 6 Nov. 1977, pp. 786–794, XP000617508, Moranville M.B. & AL.: "Dispersion in Layered Porous Media" *pp. 790 & 791, "Experimental Methods"*.

*Primary Examiner*—Stanley S. Silverman
*Assistant Examiner*—Jacqueline A Ruller
*Attorney, Agent, or Firm*—Antonelli, Terry, Stout & Kraus, LLP

[57] ABSTRACT

The invention is used to manufacture an inhomogeneous medium whose porosity and permeability undergo rapid transitions from one point to another of its volume, by juxtaposing different materials without creating a barrier. Such a transition is made by juxtaposing a first material and a second material with a different porosity to the first. One of them can be a rock sample such as sandstone for example, the other can be a composite material obtained by agglomerating pyrex powder for example, the whole being heated according to a specific temperature cycle up to a temperature (TR) lower than the melting point of the two materials but sufficient to achieve partial melting of one of the materials at the interface with the other material, but without formation of a continuous or discontinuous capillary barrier between them, or an interzone with preferred passage for fluids. Thus, different composite materials can be juxtaposed to constitute the inhomogeneous medium. The invention has applications to manufacturing a model representative of reservoir rocks in order to test assisted hydrocarbon recovery methods.

18 Claims, 1 Drawing Sheet

METHOD OF MANUFACTURING A POROUS INHOMOGENEOUS MATERIAL

BACKGROUND OF THE INVENTION

1. Field of the Invention

The present invention relates to a method of manufacturing an inhomogeneous porous material and a transparent physical model allowing the behavior of samples in response to injected fluids to be simulated and visualized in the laboratory.

Such a model is useful for example when studying in the laboratory the displacement of multiphase fluids in a porous medium with similar characteristics to those of rocks of underground deposits that may contain hydrocarbons.

2. Description of the Prior Art

It is known in the industry that agglomerates, that can be obtained for example by sintering particles of specific sizes such as ceramic powders and glass, metal, etc. microbeads, can be made for wide-ranging applications. In this way, blocks whose porosity is relatively homogenous, or composites that combine agglomerates made from different substances, are formed. One example of a known process for manufacturing an inhomogeneous material for a heat insulator by sintering metal powders and ceramic powders is described in Patent WO/8505352.

SUMMARY OF THE INVENTION

A method according to the invention relates to the manufacture of an inhomogeneous medium whose porosity varies, by rapid transition from one point to another in the medium, by juxtaposing at least two porous materials.

With the invention in that the temperature of the assembly formed by these materials is gradually varied according to a cycle with a predefined variation, the maximum temperature of the cycle being lower than the melting point of the lowest-melting porous material but sufficient to achieve partial melting of this lowest-melting material in order to obtain a thin interface having a substantially continuous and homogenous variation in porosity between the two materials.

The method according to the invention affords a rapid transition of porosity with no formation between the materials of a continuous or discontinuous capillary barrier or an interzone in which fluids can preferentially pass.

The slow softening obtained brings about relatively homogeneous welding of the grains with each other without filling up the voids between them.

According to a first embodiment, the temperature variation cycle is applied to a medium formed by juxtaposing a naturally porous mineral such as sandstone and a composite material obtained by agglomerating a powder.

According to another embodiment, the temperature variation cycle is applied to a medium formed by juxtaposing two composite materials.

According to another embodiment, the temperature variation cycle is applied to a medium formed by juxtaposing two minerals with different porosities, with interposition of a composite material between them.

According to one embodiment, an inhomogeneous block is made by juxtaposing, in a container for example, at least two volumes of materials with different porosities and melting points, then placing the container in an oven whose temperature is programmed to rise gradually to a sufficient temperature to soften the lowest-melting porous material during a first time interval, holding this temperature for a second specific time interval, and lowering it more gradually down to room temperature in a third time interval. The porous material that has softened constitutes a means of bonding the materials, preventing formation for example of an air space that would constitute a capillary barrier and preventing formation of an interzone constituting a preferred passage for fluids.

For example, the juxtaposition of a natural porous material such as sandstone and a composite material such as sintered glass can be used, in which case the oven holding temperature is approximately 750° C. and the lengths of the first, second, and third time intervals are approximately 3 hours, 1 hour, and 20 hours, respectively.

The composite material can also be an agglomerate of glass balls of specific porosity.

The method according to the invention allows a model of an inhomogeneous medium to be obtained simply at low cost, with a specific configuration of zones with well-defined porosities for developing methods of assisted hydrocarbon recovery from underground deposits.

BRIEF DESCRIPTION OF THE DRAWINGS

Other characteristics and advantages of the method according to the invention will emerge from reading the description hereinbelow with reference to the attached drawings wherein.

DESCRIPTION OF THE PREFERRED EMBODIMENT

Figure 1:
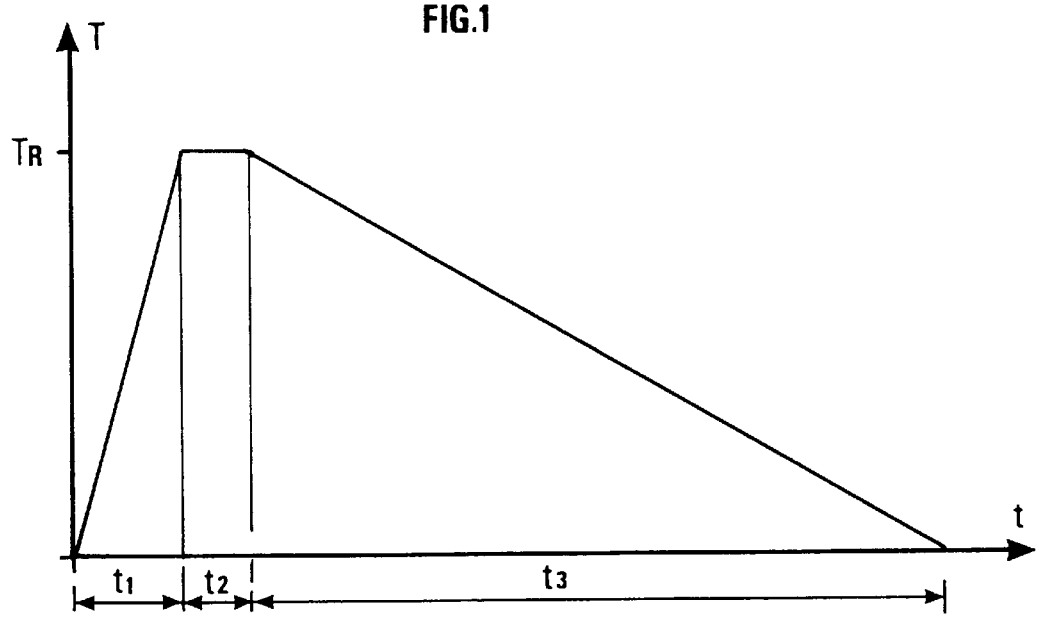
FIG. 1 shows the change in temperature in an assembly of materials for forming continuous capillary transitions at each interface.

Blocks are created for example by juxtaposing a first and a second material in a container. The container is placed in an oven under the control of a microcomputer programmed to adjust the temperature of the oven to the curve shown in FIG. 1. In the first time interval, the oven temperature is gradually raised for a time t1 from room temperature to a temperature TR less than the melting point of the two materials but sufficient to achieve softening and/or partial melting of one of the materials. This temperature is held for a time t2 then decreases to return gradually to room temperature. This return is slower and is spread over a time interval t3.

Figure 2:
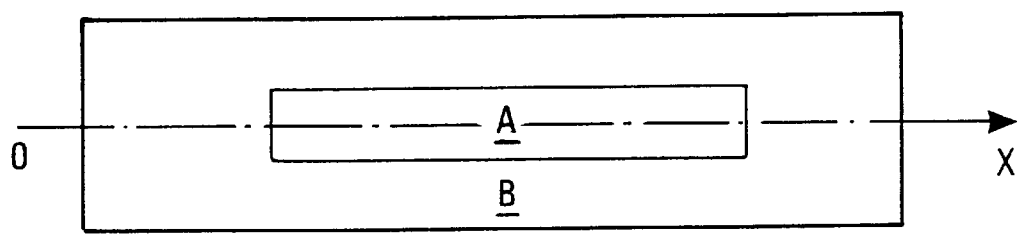
FIG. 2 shows an assembly of a sample of a first material included in a block in a second material.

For example, as shown in FIG. 2 a volume of agglomerate pyrex powder A whose melting point is approximately 800° C. is included inside a bar B of sandstone (Vosges sandstone or Fontainebleau sandstone for example). The temperature TR chosen is approximately 750° C. and the time intervals t1, t2, and t3 are approximately 3 h, 1 h, and 20 h, respectively.

Figure 3:
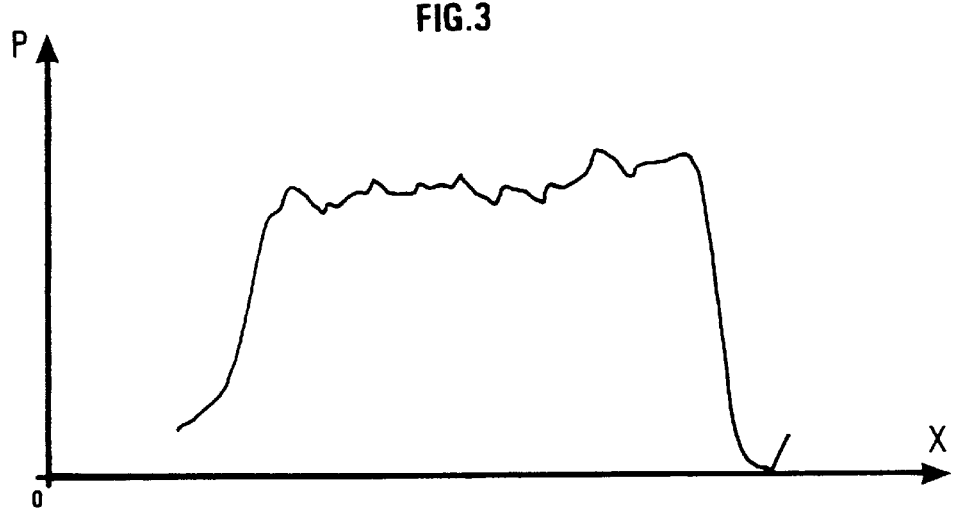
FIG. 3 is a graph of the change in porosity P along axis OX with two fast transition zones at the interfaces between the two materials.

The result is the creation of a thin, capillary fast-transition zone which is continuous along the interface, as shown by the porosity change curve (FIG. 3) at the interfaces between the two samples A, B shown schematically in FIG. 2.

Thus, a series of strata with different porosities and permeabilities can be obtained, suitable for building a laboratory model to test the displacement of multiphase fluids in relatively permeable media as found in oil-bearing deposits.

For example, a sample of sandstone is cut and shaped, and a powdered material is spread thereon and compacted with a degree of pressure that varies according to the desired degree of porosity. Another sample of relatively porous rock can be superimposed on the previous block of powder, itself if need be covered with a new powder agglomerate, either of the same type as the previous agglomerate or different. Thus, a stratified medium can be obtained as desired with multiple alternating layers changing according to the nature of the rocks and powdered materials used and/or to the technique of compacting the powders used.

A temperature TR that is less then but close to the melting point of the lowest-melting material is always chosen in order to achieve this partial melting.

Composite materials such as glass particles with well-defined particle size, cellular concrete, etc. can also be used as materials for making heterogenous media with different porosities and permeabilities.

Inhomogeneous medium are made by combining either composite materials with different softening points or samples of relatively porous rock and composite materials, or samples of rock with different porosities between which a thin layer of a composite which, by partial melting, eliminates any air space between them that could create a sealed continuous or discontinuous barrier is preferably interposed.

We claim:

1. A method of manufacturing an inhomogeneous medium having a porosity which varies discontinuously with a volume of the medium comprising:

combining first and second porous materials to form an assembly of the materials by juxtaposing a naturally porous material and a composite material; and varying temperature of the assembly in a temperature cycle; and wherein the temperature cycle having a maximum temperature lower than a melting point of a lowest melting material of the first and second materials but which is sufficient to achieve partial melting of the lowest melting of the first and second materials; and the partial melting produces an interface between the assembly of materials having a substantially continuous and homogenous porosity variation.

2. A method of manufacturing an inhomogeneous medium having a porosity which varies discontinuously with a volume of the medium comprising:

combining first and second porous materials to form a homogenous block with the first material having a partial melting point different than the second material; and placing the homogenous block in an oven having a programmed temperature which raises a temperature of the homogenous block gradually to reach a partial melting point of the first or second porous material with a lowest melting point during a first time interval, holding a temperature of the homogenous block at a temperature at which the partial melting occurs for a second time interval, lowering temperature of the oven from the temperature at which partial melting occurs gradually down to ambient temperature during a third time interval with the third time interval being longer than the first time interval; and wherein the partial melting produces an interface between the first and second materials of the homogeneous block having a substantially continuous and homogenous porosity variation.

3. A method according to claim 1 further comprising:

placing the assembly in a container; and placing the container in an oven having a programmed temperature cycle to produce the temperature cycle, the temperature cycle in the oven raising the temperature of the oven gradually to reach a temperature at which the partial melting occurs during a first time interval, holding a temperature of the oven at a temperature at which the partial melting occurs for a second time interval and lowering a temperature of the oven from a temperature at which the partial melting occurs gradually down to ambient temperature during a third time interval with the third time interval being longer than the first time interval to produce the interface.

4. A method in accordance with claim 1 wherein the naturally porous material is sandstone.

5. A method according to claim 1 wherein the temperature cycle is applied to the assembly formed with another composite material disposed between the first and second porous material.

6. A method according to claim 4 further comprising:

placing the assembly in a container; and placing the container in an oven having a programmed temperature cycle to produce the temperature cycle, the temperature cycle in the oven raising the temperature of the oven gradually to reach a temperature at which the partial melting occurs during a first time interval, holding a temperature of the oven at a temperature at which the partial melting occurs for a second time interval and lowering a temperature of the oven from a temperature at which the partial melting occurs gradually down to ambient temperature during a third time interval with the third time interval being longer than the first time interval to produce the interface.

7. A method according to claim 5 further comprising:

placing the assembly in a container; and placing the container in an oven having a programmed temperature cycle to produce the temperature cycle, the temperature cycle in the oven raising the temperature of the oven gradually to reach a temperature at which the partial melting occurs during a first time interval, holding a temperature of the oven at a temperature at which the partial melting occurs for a second time interval and lowering a temperature of the oven from a temperature at which the partial melting occurs gradually down to ambient temperature during a third time interval with the third time interval being longer than the first time interval to produce the interface.

8. A method according to claim 1 wherein the assembly is a homogeneous block made by juxtaposing, in a container, at least one volume of the first material with at least one volume of the second material having a partial melting point different from that of the first material, the temperature cycle being achieved by placing the container in an oven having a programmed temperature which rises gradually to a temperature sufficient to reach a partial melting point of the porous material with the lowest melting point during a first time interval (t1), holding this temperature for a second specific time interval (t2), and lowering it more gradually down to room temperature in a third time interval (t3).

9. A method according to claim 1 wherein the assembly is a homogeneous block made by juxtaposing, in a container, at least one volume of the first material with at least one volume of the second material having a partial melting point different from that of the first material, the temperature cycle being achieved by placing the container in an oven having a programmed temperature which rises gradually to a temperature sufficient to reach a partial melting point of the porous material with the lowest melting point during a first time interval (t1), holding this temperature for a second time interval (t2), and lowering the temperature down to room temperature in a third time interval (t3) which is longer than the first time interval (t1).

10. A method according to claim 4 wherein the assembly is a homogeneous block made by juxtaposing, in a container, at least one volume of the first material with at least one volume of the second material having a partial melting point different from that of the first material, the temperature cycle being achieved by placing the container in an oven having a programmed temperature which rises gradually to a temperature sufficient to reach a partial melting point of the porous material with the lowest melting point during a first time interval (t1), holding this temperature for a second time interval (t2), and lowering the temperature down to room temperature in a third time interval (t3) which is longer than the first time interval (t1).

11. A method according to claim 5 wherein the assembly is a homogeneous block made by juxtaposing, in a container, at least one volume of the first material with at least one volume of the second material having a partial melting point different from that of the first material, the temperature cycle being achieved by placing the container in an oven having a programmed temperature which rises gradually to a temperature sufficient to reach a partial melting point of the porous material with the lowest melting point during a first time interval (t1), holding this temperature for a second time interval (t2), and lowering the temperature down to room temperature in a third time interval (t3) which is longer than the first time interval (t1).

12. A method according to claim 1, wherein the first material is a sample of porous rock, the second material is made of sintered glass, the partial melting point is approximately 750° C.

13. A method according to claim 2, wherein the first material is a sample of porous rock, the second material is made of sintered glass, the partial melting point is approximately 750° C., and a length of the first, second, and third time intervals are approximately 3 hours, 1 hour, and 20 hours, respectively.

14. A method according to claim 3, wherein the first material is a sample of porous rock, the second material is made of sintered glass, the partial melting point is approximately 750° C., and a length of the first, second, and third time intervals are approximately 3 hours, 1 hour, and 20 hours, respectively.

15. A method according to claim 6, wherein the first material is a sample of porous rock, the second material is made of sintered glass, the partial melting point is approximately 750° C., and a length of the first, second, and third time intervals are approximately 3 hours, 1 hour, and 20 hours, respectively.

16. A method according to claim 7, wherein the naturally porous material is a sample of porous rock, the composite material is sintered glass, the partial melting point is approximately 750° C., and a length of the first, second, and third time intervals are approximately 3 hours, 1 hour, and 20 hours, respectively.

17. A method according to claim 1 wherein the composite material is an agglomerate of glass particles.

18. A method according to claim 1 wherein the inhomogeneous medium has zones of different porosities and permeabilities and is used for developing methods of assisted hydrocarbon recovery from underground deposits.

* * * * *